US00PP30201P3

(12) United States Plant Patent
Klemm et al.

(10) Patent No.: US PP30,201 P3
(45) Date of Patent: Feb. 12, 2019

(54) ***CALIBRACHOA* PLANT NAMED 'KLECA16316'**

(50) Latin Name: ***Calibrachoa* sp.**
Varietal Denomination: KLECA16316

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/731,834

(22) Filed: Aug. 9, 2017

(65) Prior Publication Data

US 2018/0279532 P1 Sep. 27, 2018

(30) Foreign Application Priority Data

Mar. 27, 2017 (CA) ..... PBR 17-9143

(51) Int. Cl.
*A01H 5/02* (2018.01)
*A01H 6/82* (2018.01)

(52) U.S. Cl.
USPC ..... Plt./413
CPC ..... *A01H 6/821* (2018.05); *A01H 5/02* (2013.01)

(58) Field of Classification Search
USPC ..... Plt./413
CPC ..... A01H 5/02
See application file for complete search history.

(56) References Cited

PUBLICATIONS https://www.dickmanfarms.com/assets/Uploads/documents/DF-2014-15-SP.pdf; 2014-2015; 1 page.*
http://www.lucasgreenhouses.com/plant/Calibrachoa-hybrid-Minifamous-Neo-Royal-Blue; 2018; 2 pages.*
http://www.ball.com.br/wp-content/uploads/2016/11/Ball-Seed-New-Varieties-2017.pdf; 2017; 1 page.*

* cited by examiner

*Primary Examiner* — Kent L Bell
(74) *Attorney, Agent, or Firm* — Bethany R. Roahrig; Cochran Freund & Young LLC

(57) ABSTRACT

A new *Calibrachoa* plant particularly distinguished by dark purple flowers and a semi-upright, vigorous plant habit, is disclosed.

1 Drawing Sheet

Genus and species: *Calibrachoa* sp.
Variety denomination: 'KLECA16316'.

CROSS REFERENCE TO RELATED APPLICATIONS

The present application claims priority to Canadian Plant Breeder's Rights Application number 17-9143, as filed on Mar. 27, 2017. Plant Breeder's Rights for 'KLECA16316' were also applied for in Europe on Jun. 30, 2017 (Application number 2017-1692). 'KLECA16316' has not been made publicly available or sold more than one year prior to the effective filing date of this application.

BACKGROUND OF THE NEW PLANT

The present invention comprises a new and distinct variety of *Calibrachoa*, botanically known as *Calibrachoa* sp., and hereinafter referred to by the variety name 'KLECA16316'. 'KLECA16316' originated from a controlled cross conducted in Stuttgart, Germany in the summer of 2012, between the proprietary female *Calibrachoa* variety 'CA-2011-0593' (unpatented) and the proprietary male *Calibrachoa* variety 'CA-2011-0572' (unpatented).

The seeds were sown and plants were grown for evaluation. A plant was selected in May 2012 which had dark purple flowers and was subsequently named 'KLECA16316'. In May 2012, 'KLECA16316' was first vegetatively propagated by tip cuttings in Stuttgart, Germany. 'KLECA16316' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Dark purple colored flowers; and
2. A semi-upright and vigorous plant habit.

DESCRIPTION OF THE PHOTOGRAPH

This new *Calibrachoa* plant is illustrated by the accompanying photograph which shows the flowers and foliage of the plant. The photograph is of an eight-week-old plant grown in a greenhouse in Stuttgart, Germany in May 2014. The colors shown are as true as can be reasonably obtained by conventional photographic procedures.

DESCRIPTION OF THE NEW VARIETY

The following detailed descriptions set forth the distinctive characteristics of 'KLECA16316'. The data which define these characteristics were collected from asexual reproductions carried out in Stuttgart, Germany. Data was collected on 20 week old plants grown outdoors in Stuttgart, Germany in June 2017. Color references are to The R.H.S. Colour Chart of The Royal Horticultural Society of London (R.H.S.), 5th edition (2007).

Classification:
- *Family.*—Solanaceae.
- *Species.*—*Calibrachoa* sp.
- *Common name.*—*Calibrachoa.*

Parentage:
- *Female.*—Proprietary *Calibrachoa* 'CA-2011-0593' (unpatented).
- *Male.*—Proprietary *Calibrachoa* 'CA-2011-0572' (unpatented).

Plant description:
- *Life cycle.*—Annual.
- *Form.*—Short-lived subshrubs.
- *Habit.*—Semi-upright, vigorous.
- *Height* (*from soil line to top of foliage*).—20.0 cm.
- *Spread.*—62.0 cm.

Propagation: Vegetatively propagated.
- *Type cuttings.*—Tip cuttings.
- *Time to produce a rooted cutting.*—3 weeks.

Stems:
- *Stem color.*—RHS 144C.
- *Pubescence.*—Absent.
- *Stem diameter.*—0.3 cm to 0.5 cm.
- *Stem length.*—40.0 cm. From soil line to first node: 2.0 cm.
- *Internode length.*—2.0 cm to 3.0 cm.

Leaves:
- *Arrangement.*—Opposite.
- *Shape.*—Elliptic to lanceolate.
- *Apex.*—Broadly acute.
- *Base.*—Attenuate.
- *Margin.*—Ciliate.
- *Surface.*—Smooth.
- *Surface pubescence.*—Absent.
- *Venation.*—Arcuate.
- *Venation color.*—Upper surface: RHS 144C. Lower surface: RHS 144D.
- *Length.*—2.2 cm.
- *Width.*—0.6 cm.
- *Color.*—Upper surface: RHS 137B. Lower surface: RHS 137D.
- *Fragrance.*—Absent.

Flowers:
- *Flowering habit.*—Single flowers.
- *Flower type.*—Determinate inflorescence.
- *Flowering requirements.*—A minimum of light sun is required.
- *Duration of flowers.*—6 days.
- *Corolla.*—Smooth texture.
- *Shape.*—Funnel form.
- *Fragrance.*—Absent.

Flower buds:
- *Surface.*—Smooth.
- *Length.*—1.9 cm.
- *Diameter.*—0.3 cm.
- *Shape.*—Irregular to oblong.
- *Color.*—RHS N92A.

Peduncle:
- *Length.*—1.3 cm.
- *Diameter.*—0.1 cm.
- *Color.*—RHS 145A.
- *Texture.*—Smooth.
- *Anthocyanin color.*—Occasionally present; RHS N200A.

Flower description:
- *Flower depth.*—2.7 cm.
- *Flower tube length.*—1.5 cm.
- *Flower tube diameter.*—0.9 cm.
- *Flower diameter.*—3.9 cm.
- *Pedicel color.*—RHS 145B.
- *Pedicel length.*—1.3 cm.
- *Pedicel diameter.*—0.1 cm.
- *Calyx.*—Funnel-shaped.

Sepals:
- *Shape.*—Lanceolate.
- *Apex.*—Acute.
- *Margin.*—Entire.
- *Length.*—1.2 cm.
- *Diameter.*—0.3 cm.
- *Sepal color.*—Upper surface: RHS 143A. Lower surface: RHS 143C.

Petals:
- *Shape.*—Obcordate.
- *Length.*—1.8 cm.
- *Apex.*—Truncate to emarginate.
- *Margin.*—Entire.
- *Base.*—Open and fused in the tube.
- *Pubescence.*—Absent.
- *Lobe length.*—1.8 cm.
- *Lobe width.*—1.8 cm.
- *Color.*—Lobe color: Upper surface: RHS 83A when first opened; RHS 83B when fully opened; RHS 203A is the main color at the transition to corolla tube area; strong conspicuous veins colored RHS 103A and midveins colored RHS 203A. Lower surface: RHS 83C; medium conspicuous veins colored RHS 103A and midveins colored RHS 203A. Corolla tube color: Inner: RHS 14C with medium conspicuous veins. Outer: RHS 14D with medium conspicuous veins.
- *Fragrance.*—Absent.

Reproductive organs:
- *Stamen number.*—5. Anther color: RHS 7A. Filament color: RHS 145C. Filament length.—0.7 cm. Pollen color: RHS 7A.
- *Ovary.*—Placenta arrangement: Ovate. Pistil number: 1. Pistil length: 0.8 cm. Stigma color: RHS 143B. Style length: 0.6 cm. Style color: RHS 150C.

Fruit/seed set: Seed is sometimes observed but additional information is not available.

Disease/insect resistance: None observed.

COMPARISON WITH PARENTAL LINES AND KNOWN VARIETY

'KLECA16316' is distinguished from its parents as described in Table 1:

TABLE 1

Comparison with Parental Lines

| Trait | Variety 'KLECA16316' | Female parent 'CA-2011-0593' | Male parent 'CA-2011-0572' |
|---|---|---|---|
| Flower area of main color at transition to corolla tube | Medium | Small | Small |

TABLE 1-continued

| Comparison with Parental Lines | | | |
|---|---|---|---|
| Trait | Variety 'KLECA16316' | Female parent 'CA-2011-0593' | Male parent 'CA-2011-0572' |
| Flower color intensity | In between 'CA-2011-0593' and 'CA-2011-0572' | Lighter than 'KLECA16316' | Darker than 'KLECA16316' |

'KLECA16316' is most similar to the *Calibrachoa* plant named MINIFAMOUS 'Compact Blue', also known as 'KLECA12236' (U.S. Plant Pat. No. 25,887). Differences between the two varieties are described in Table 2:

TABLE 2

| Comparison with Similar Variety | | |
|---|---|---|
| Trait | Variety 'KLECA16316' | Commercial line 'KLECA12236' |
| Main flower color | RHS 83B when fully opened | RHS 87A |

We claim:

1. A new and distinct variety of *Calibrachoa* plant named 'KLECA16316' as illustrated and described herein.

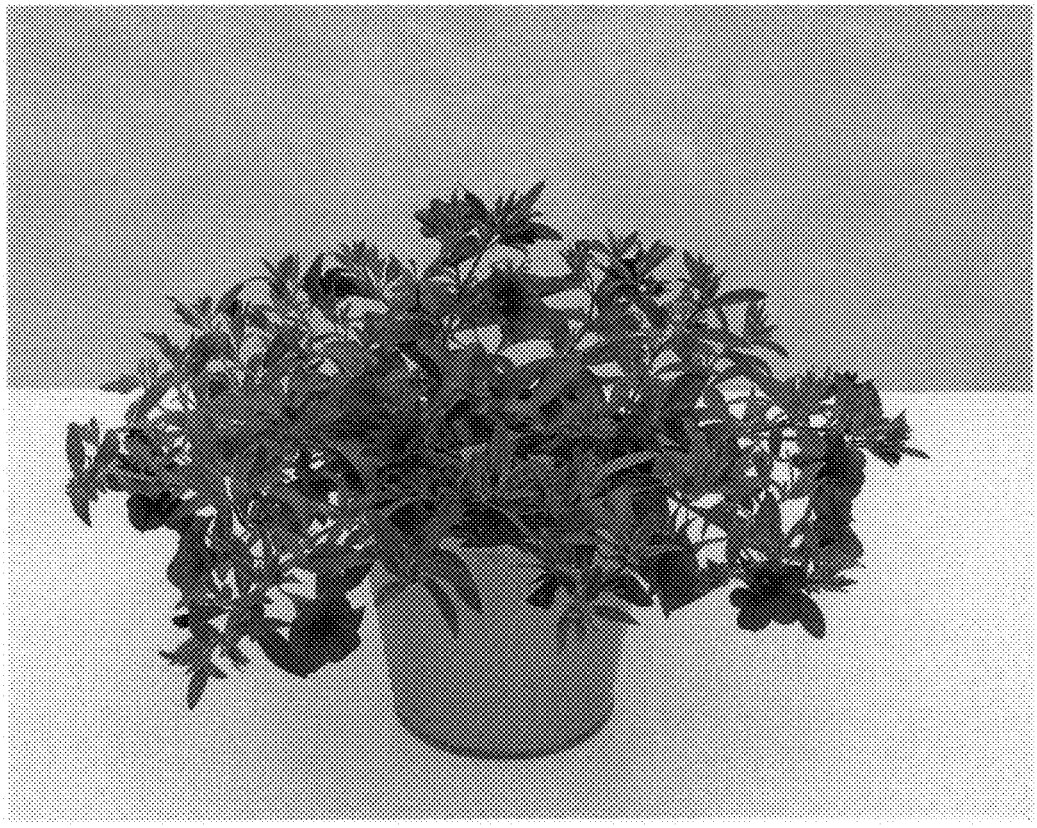

* * * * *